US012633405B2

(12) United States Patent (10) Patent No.: US 12,633,405 B2
Srivastava et al. (45) Date of Patent: May 19, 2026

(54) ADJUSTABLE HEALTHCARE-RELATED DATA COLLECTION

(71) Applicant: Boston Scientific Neuromodulation Corporation, Valencia, CA (US)

(72) Inventors: Kyle Harish Srivastava, Saint Paul, MN (US); Bradley Lawrence Hershey, Carrollton, TX (US); Benjamin Phillip Hahn, Austin, TX (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 335 days.

(21) Appl. No.: 17/943,952

(22) Filed: Sep. 13, 2022

(65) Prior Publication Data

US 2023/0097509 A1 Mar. 30, 2023

Related U.S. Application Data

(60) Provisional application No. 63/249,729, filed on Sep. 29, 2021.

(51) Int. Cl.
*G16H 40/63* (2018.01)
(52) U.S. Cl.
CPC .................................. *G16H 40/63* (2018.01)
(58) Field of Classification Search
CPC ......... G16H 40/63; G16H 20/30; G16H 10/20
See application file for complete search history.

(56) References Cited

U.S. PATENT DOCUMENTS

2007/0213040 A1* 9/2007 Itou ................... H04W 52/0274
455/419
2015/0305689 A1* 10/2015 Gourmelon ........... A61B 5/1118
600/301
2018/0193652 A1 7/2018 Srivastava et al.
2019/0022397 A1 1/2019 Srivastava et al.
2021/0065855 A1 3/2021 Pepin et al.

FOREIGN PATENT DOCUMENTS

WO WO-2020092701 A2 5/2020
WO WO-2023055563 A1 4/2023

OTHER PUBLICATIONS

"International Application Serial No. PCT/US2022/043369, International Preliminary Report on Patentability mailed Apr. 11, 2024", 7 pgs.

(Continued)

*Primary Examiner* — Reginald R Reyes
(74) *Attorney, Agent, or Firm* — Schwegman Lundberg & Woessner. P.A.

(57) ABSTRACT

A system may include at least one data collection platform and an event detector configured to detect an event. The at least one data collection platform may be configured for use to collect healthcare-related data at a defined data resolution for transfer to a data receiving system that may include one or more processors, at least one data input for receiving healthcare-related data, and memory for storing instructions for implementation by the one or more processors to collect healthcare-related data via the at least one data input. The at least one data collection platform may be configured to change the data resolution for collecting healthcare-related data in response to the detected event.

19 Claims, 8 Drawing Sheets

(56)         References Cited

OTHER PUBLICATIONS

"International Application Serial No. PCT/US2022/043369, International Search Report mailed Jan. 2, 2023", 4 pgs.
"International Application Serial No. PCT/US2022/043369, Written Opinion mailed Jan. 2, 2023", 5 pgs.
"European Application Serial No. 22786860.1, Response to Communication Pursuant to Rules 161 and 162 filed Nov. 12, 2024", 10 pgs.

* cited by examiner

ELECTRODES

326

MEDICAL DEVICE
(E.G., ELECTRICAL THERAPY
DEVICE SUCH AS
A NEUROMODULATION DEVICE)

317

PROGRAMMING
DEVICE

USER
INTERFACE

318

321

325

AMBULATORY MEDICAL DEVICE
(E.G. IMPLANTABLE OR WEARABLE)

DBS EXAMPLE

SCS EXAMPLE

425

417

EXTERNAL SYSTEM

418

427

426

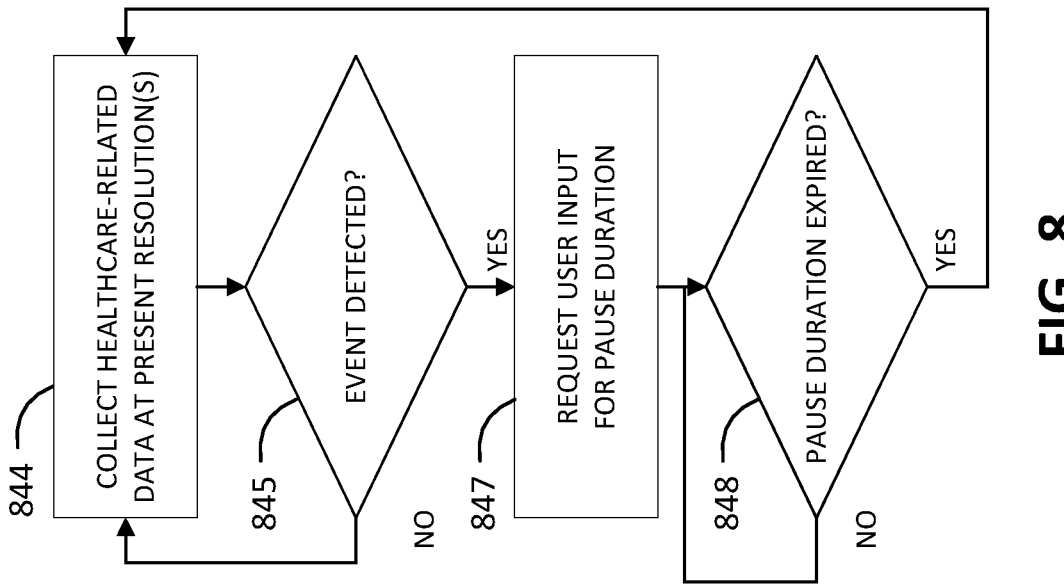

844 — COLLECT HEALTHCARE-RELATED DATA AT PRESENT RESOLUTION(S)

845 — EVENT DETECTED?

NO

YES

847 — REQUEST USER INPUT FOR PAUSE DURATION

848 — PAUSE DURATION EXPIRED?

NO

YES

FIG. 8

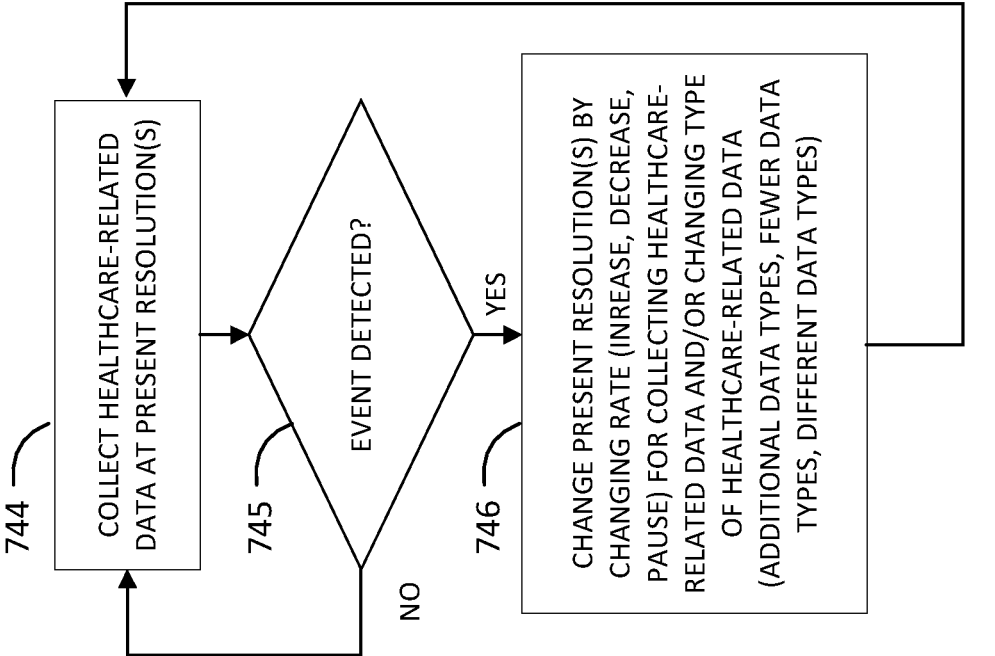

744 — COLLECT HEALTHCARE-RELATED DATA AT PRESENT RESOLUTION(S)

745 — EVENT DETECTED?

NO

YES

746 — CHANGE PRESENT RESOLUTION(S) BY CHANGING RATE (INREASE, DECREASE, PAUSE) FOR COLLECTING HEALTHCARE-RELATED DATA AND/OR CHANGING TYPE OF HEALTHCARE-RELATED DATA (ADDITIONAL DATA TYPES, FEWER DATA TYPES, DIFFERENT DATA TYPES)

FIG. 7

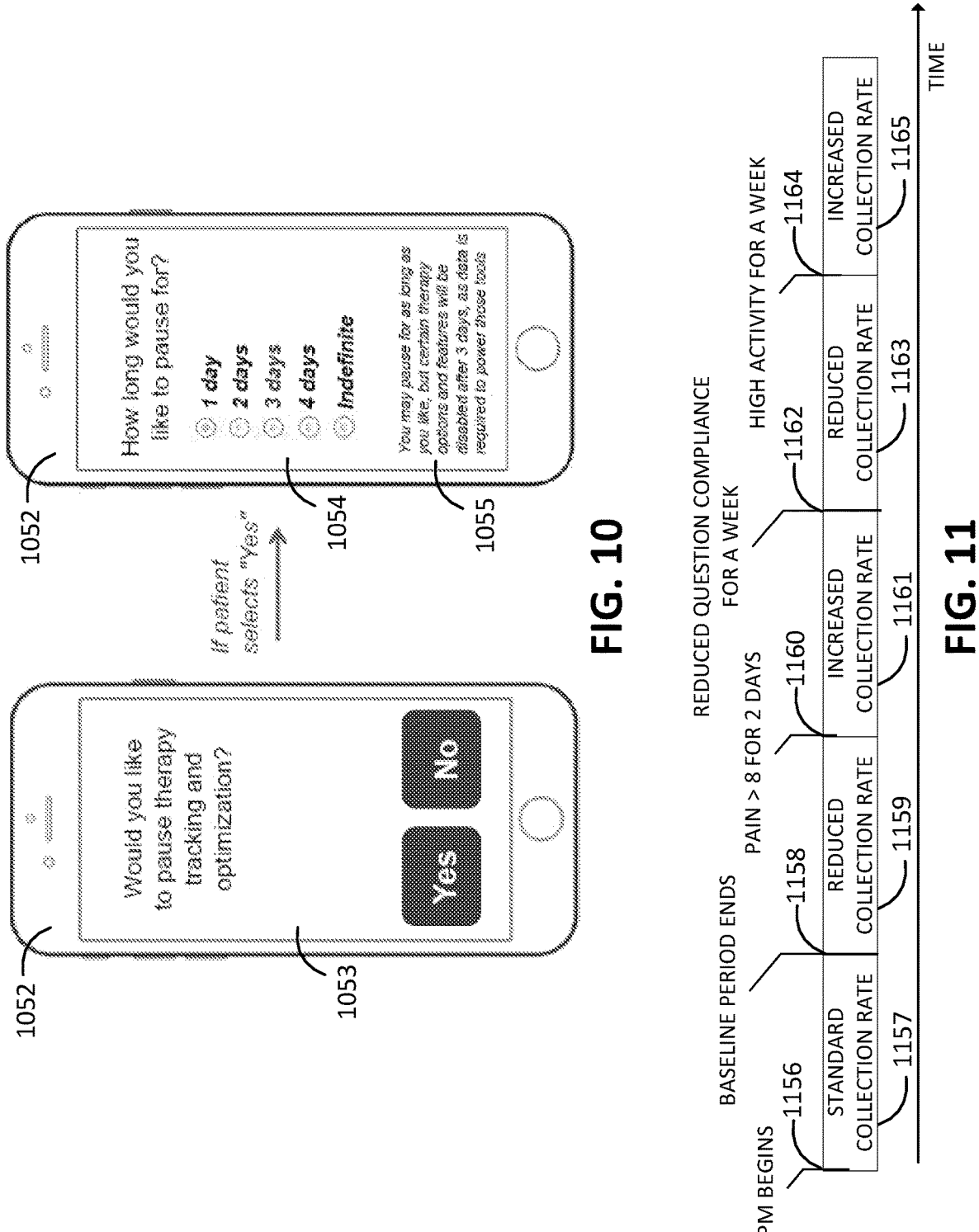

Would you like to pause therapy tracking and optimization?

Yes    No

1053

*If patient selects "Yes"*

1052

How long would you like to pause for?

1 day
2 days
3 days
4 days
Indefinite

1054

You may pause for as long as you like, but certain therapy options and features will be disabled after 3 days, as data is required to power those tools

RPM BEGINS — 1156
BASELINE PERIOD ENDS — 1158
PAIN > 8 FOR 2 DAYS — 1160
REDUCED QUESTION COMPLIANCE FOR A WEEK — 1162
HIGH ACTIVITY FOR A WEEK — 1164

STANDARD COLLECTION RATE — 1157
REDUCED COLLECTION RATE — 1159
INCREASED COLLECTION RATE — 1161
REDUCED COLLECTION RATE — 1163
INCREASED COLLECTION RATE — 1165

TIME

ADJUSTABLE HEALTHCARE-RELATED DATA COLLECTION

CLAIM OF PRIORITY

This application claims the benefit of U.S. Provisional Application No. 63/249,729, filed on Sep. 29, 2021, which is hereby incorporated by reference in its entirety.

TECHNICAL FIELD

This document relates generally to medical systems, and more particularly, but not by way of limitation, to systems, devices, and methods for adjusting collection of healthcare-related data.

BACKGROUND

Healthcare relates to the preservation of health (e.g., preservation of mental and/or physical) by preventing, treating or managing illness. A trend in healthcare is to collect and analyze large amounts of data, referred to herein as "healthcare-related data" as it is data useful for providing or analyzing healthcare. For example, remote patient monitoring may be used to provide large amounts of healthcare-related data at the fingertips of both patients and healthcare providers.

Some systems are configured solely as a data collection system for purpose of collecting and transferring data. Other systems combine data collection with a therapy. For example, a system may include a data collection platform and at least one medical device that is configured to deliver a therapy such as an electrical or drug therapy. A non-limiting example of a medical device to deliver a drug therapy is an insulin pump, and non-limiting examples of a medical device configured to deliver electrical therapy muscle stimulators, cardiac rhythm devices such as pacemakers and defibrillators, and neurostimulators. Examples of neuromodulation include Spinal Cord Stimulation (SCS), Deep Brain Stimulation (DBS), Peripheral Nerve Stimulation (PNS), and Functional Electrical Stimulation (FES). Physiological signal(s) may be sensed for various reasons related to the delivered therapy, such as to time the therapy delivery, to determine enabling or disabling conditions for delivering the therapy, to determine an efficacy of a therapy, or to provide feedback for closed-loop control of the therapy. In some non-limiting examples, glucose readings from a continuous glucose monitor may be used to provide closed-loop control of an insulin pump, and action potentials within a nerve may be sensed to provide closed-loop control of a neuromodulation therapy. Such systems may also be configured to receive user inputted data, such as but not limited to diet, carb counts or exercise information for the insulin pump systems or pain-related data for a neuromodulation (e.g., spinal cord stimulation) therapy.

However, there are also reasons to either stop or reduce data collection. For example, data collection can become burdensome on the patient, on the data collection platform or both. The patient may find that it is overwhelming and tedious to answer questions, or user interaction that may be required to collect physiological data may be complicated and/or tiresome. Patients who have dexterity or vision issues, such as many older patients, may find it difficult to provide the user input. Even if physiological data is collected without requiring user interaction, such data collection can require significant power/battery drain, processing, data storage and data transmission, which may increase the size, cost and complexity of the system, especially if the data collection is at a high resolution.

SUMMARY

An example (e.g., "Example 1") of a system may include at least one data collection platform and an event detector configured to detect an event. The at least one data collection platform may be configured for use to collect healthcare-related data at a defined data resolution for transfer to a data receiving system that may include one or more processors, at least one data input for receiving healthcare-related data, and memory for storing instructions for implementation by the one or more processors to collect healthcare-related data via the at least one data input. The at least one data collection platform may be configured to change the data resolution for collecting healthcare-related data in response to the detected event.

In Example 2, the subject matter of Example 1 may optionally be configured such that the change to the data resolution includes an increase or a decrease in a number of healthcare-related data types to be collected.

In Example 3, the subject matter of any one or more of Examples 1-2 may optionally be configured such that the change to the data resolution includes collecting a second type of healthcare-related data in place of collecting a first type of healthcare-related data.

In Example 4, the subject matter of any one or more of Examples 1-3 may optionally be configured such that the change to the data resolution includes an increase or decrease in a number of data-collection instances for collecting healthcare-related data over a period of time. Instances for collecting healthcare-related data may cover a constant collection rate where a same interval occurs between data collection instances, or may be intermittent data collection instances at non-regular intervals.

In Example 5, the subject matter of any one or more of Examples 1-4 may optionally be configured such that the at least one data collection platform may be configured to collect objective data and may be configured to collect subjective data for the patient. The change to the data resolution may include a switch from collecting the objective data to collecting the subjective data or from collecting the subjective data to collecting the objective data.

In Example 6, the subject matter of any one or more of Examples 1-5 may optionally be configured such that the at least one data collection platform may be configured to use one or more sensors to detect objective patient data, and the change to the data resolution may include a change to a number of sensors used to detect objective patient data or a replacement of at least one of the one or more sensors with another sensor to detect other patient data.

In Example 7, the subject matter of any one or more of Examples 1-6 may optionally be configured such that the at least one data collection platform may be configured to use at least one user interface to receive subjective patient data by requesting the patient to answer at least one question, and the change to the data resolution may include a change a number of questions to be answered by the patient.

In Example 8, the subject matter of any one or more of Examples 1-7 may optionally be configured such that the at least one data collection platform may be configured to use at least one user interface to receive subjective patient data by requesting the patient to answer at least one question, and the change to the data resolution may include a request for the patient to answer a second type of question in place of requesting the patient to answer a first type of question.

In Example 9, the subject matter of any one or more of Examples 1-8 may optionally be configured such that the at least one data collection platform may be configured to use at least one user interface to receive subjective patient data from the patient, and the event detector may be configured to detect patient compliance with providing the subjective patient data.

In Example 10, the subject matter of any one or more of Examples 1-9 may optionally be configured such that the event detector may be configured to detect patient engagement with at least one user interface used to receive subjective patient data from the patient, and the change to the data resolution may include a change to at least one of timing for asking at least one subjective question or a question type for asking the at least one subjective question.

In Example 11, the subject matter of any one or more of Examples 1-10 may optionally be configured such that at least one network may be used to transfer the collected healthcare-related data to the data receiving system.

In Example 12, the subject matter of any one or more of Examples 1-11 may optionally be configured such that the collected healthcare-related data may include data related to operational status of a medical device, data related to a therapy provided by a medical device, or patient environmental data acquired by at least one external sensor or acquired from an environmental data source. Examples of operational status may include, but are not limited to, electrode-tissue impedance, battery health or battery life, fault conditions, and the like. Examples of data related to a therapy may include the therapy program, neuromodulation parameters, timing of therapy, and the like. Examples of an environmental data source may include a weather app on a phone or other communication to access server(s).

In Example 13, the subject matter of any one or more of Examples 1-12 may optionally be configured such that the collected healthcare-related data transferred to the data receiving system may include at least one of: the event detected by the event detector; or contextual information or a time associated with at least some collected healthcare-related data.

In Example 14, the subject matter of any one or more of Examples 1-13 may optionally be configured such that the at least one data collection platform may be configured to respond to the detected event by requesting user input for a user-requested pause duration for a pause in collecting healthcare data, and to pause the collecting the healthcare-related data under the pause duration expires.

In Example 15, the subject matter of Example 15 may optionally be configured such that the system may be configured to adjust at least one system feature based on the user-inputted pause duration or flag a clinician when the user-requested pause duration exceeds a threshold or a number of patient-requested pauses exceeds a threshold.

Example 16 includes subject matter (such as a method, means for performing acts, machine readable medium including instructions that when performed by a machine cause the machine to performs acts, or an apparatus to perform). The subject matter may include collecting healthcare-related data at a defined data resolution for transfer to a data receiving system, detecting an event, and responding to the detected event by changing the data resolution for collecting healthcare-related data.

In Example 16, the subject matter of Example 15 may optionally be configured such that the changing the data resolution includes increasing or decreasing a number of healthcare-related data types to be collected.

In Example 17, the subject matter of any one or more of Examples 15-16 may optionally be configured such that the changing the data resolution includes increasing or decreasing a number of healthcare-related data types to be collected.

In Example 18, the subject matter of any one or more of Examples 15-17 may optionally be configured such that the changing the data resolution includes collecting a second type of healthcare-related data in place of collecting a first type of healthcare-related data.

In Example 19, the subject matter of any one or more of Examples 15-18 may optionally be configured such that the changing the data resolution includes increasing or decreasing a number of data-collection instances for collecting healthcare-related data over a period of time.

In Example 20, the subject matter of any one or more of Examples 15-19 may optionally be configured such that the changing the data resolution includes switching from collecting objective data to collecting subjective data or switching from collecting the subjective data to collecting the objective data.

In Example 21, the subject matter of any one or more of Examples 15-20 may optionally be configured such that the collecting healthcare-related data includes using one or more sensor(s) to detect objective patient data, and the changing the data resolution includes changing a number of sensors used to detect objective patient data or replacing at least one of the one or more sensors with another sensor to detect other patient data.

In Example 22, the subject matter of any one or more of Examples 15-21 may optionally be configured to further include using at least one user interface to receive subjective patient data by requesting the patient to answer at least one question, and the changing the data resolution includes changing a number of questions to be answered by the patient.

In Example 23, the subject matter of any one or more of Examples 15-22 may optionally be configured to further include using at least one user interface to receive subjective patient data by requesting the patient to answer at least one question, and the changing the data resolution includes changing a type of question to be answered by the patient.

In Example 24, the subject matter of any one or more of Examples 15-23 may optionally be configured to further include using at least one user interface to receive subjective patient data from the patient, and the detecting the event includes detecting patient compliance with providing the subjective patient data.

In Example 25, the subject matter of any one or more of Examples 15-24 may optionally be configured such that the detecting the event includes detecting patient engagement with at least one user interface used to receive subjective patient data from the patient, and the changing the data resolution includes changing at least one of timing or a question type for asking at least one subjective question.

In Example 26, the subject matter of any one or more of Examples 15-25 may optionally be configured to further include using at least one network to transfer the collected healthcare-related data to the data receiving system.

In Example 27, the subject matter of any one or more of Examples 15-26 may optionally be configured such that the collected healthcare-related data includes data related to operational status of a medical device, data related to a therapy provided by a medical device, or patient environmental data acquired by at least one external sensor or acquired from an environmental data source.

In Example 28, the subject matter of any one or more of Examples 15-27 may optionally be configured such that the collected healthcare-related data transferred to the data receiving system includes the detected event, or contextual information or a time associated with at least some collected healthcare-related data.

In Example 29, the subject matter of any one or more of Examples 15-28 may optionally be configured to further include responding to the detected event by requesting user input for a user-requested pause duration for a pause in collecting healthcare data, and pausing the collecting the healthcare-related data under the pause duration expires.

In Example 30, the subject matter of any one or more of Examples 15-29 may optionally be configured to further include at least one of: adjusting at least one system feature based on the user-inputted pause duration; or flagging a clinician when the user-requested pause duration exceeds a threshold or a number of patient-requested pauses exceeds a threshold.

Example 31 includes subject matter (such as a device, apparatus, or machine) that may include non-transitory machine-readable medium including instructions, which when executed by a machine, cause the machine to perform a method comprising collecting healthcare-related data at a defined data resolution for transfer to a data receiving system, detecting an event, and responding to the detected event by changing the data resolution for collecting health-care-related data.

In Example 32, the subject matter of Example 31 may optionally be configured such that the changing the data resolution includes at least one of: increasing or decreasing a number of healthcare-related data types to be collected; collecting a second type of healthcare-related data in place of collecting a first type of healthcare-related data; or increasing or decreasing a number of data-collection instances for collecting healthcare-related data over a period of time.

In Example 33, the subject matter of any one or more of Examples 31-32 may optionally be configured such that the method further comprises using at least one user interface to receive subjective patient data by requesting the patient to answer at least one question, and the changing the data resolution includes changing a number of questions to be answered by the patient.

In Example 34, the subject matter of any one or more of Examples 31-33 may optionally be configured such that the method further comprises using at least one user interface to receive subjective patient data by requesting the patient to answer at least one question, and the changing the data resolution includes changing a type of question to be answered by the patient.

In Example 35, the subject matter of any one or more of Examples 31-34 may optionally be configured such that the method further comprises using at least one user interface to receive subjective patient data from the patient, and the detecting the event includes detecting patient compliance with providing the subjective patient data.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense.

The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, a method for changing data resolution for collecting healthcare-related data in response to an event.

FIG. 8 illustrates, by way of example, a method for pausing collection of healthcare-related data.

FIG. 10 illustrates, by way of example, a user interface for requesting a user to indicate whether the collection of healthcare-related data should be paused and the length of the pause, and to provide notice that feature(s) may be adjusted because of the user-requested pause.

FIG. 11 illustrates, by way of example and not limitation, a timeline for adjusting collection rates in response to various events.

DETAILED DESCRIPTION

Figure 1:
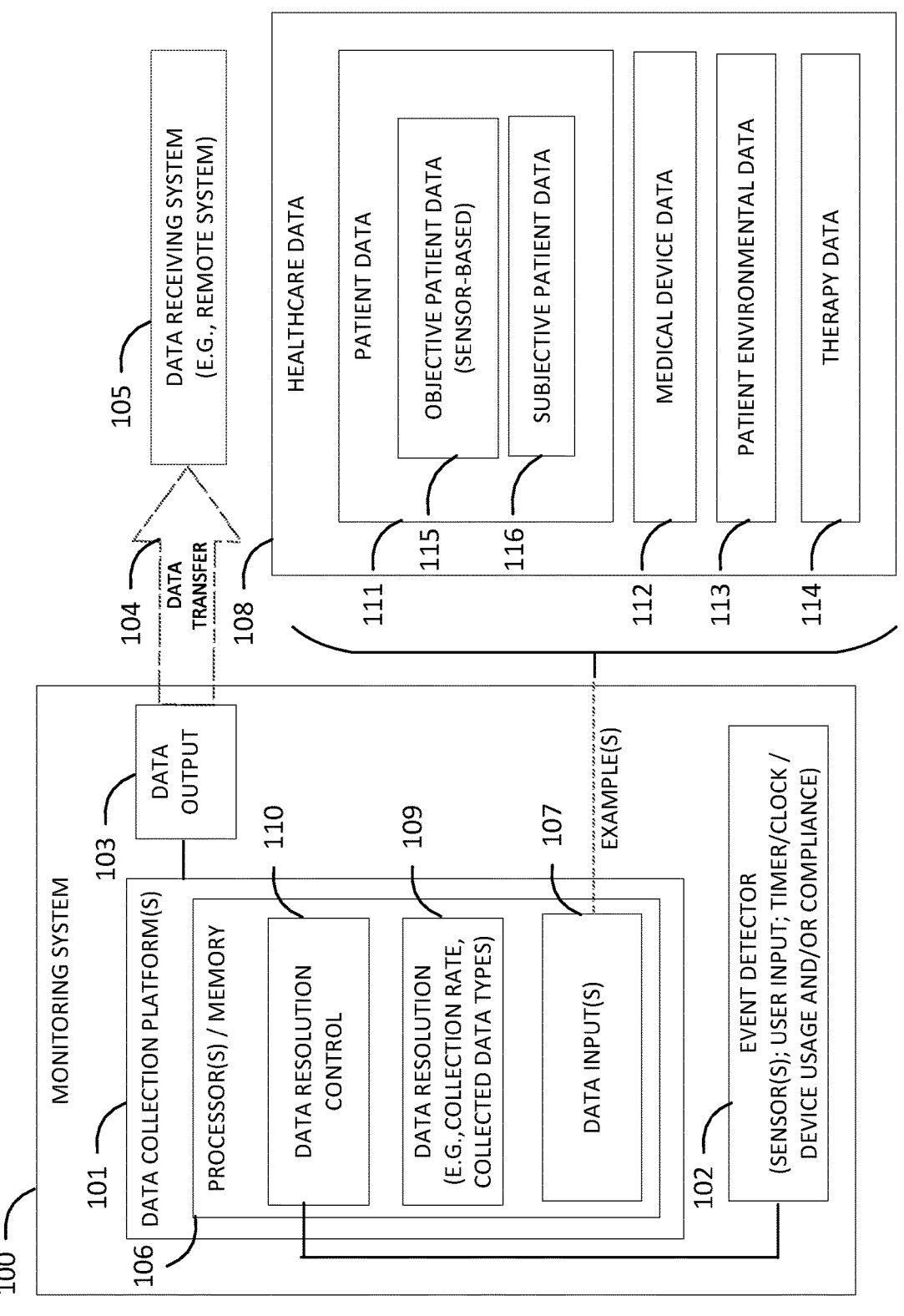
FIG. 1 illustrates, by way of example, an embodiment of a monitoring system configured for use to collect healthcare-related data for transfer to a data receiving system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments of the present subject matter modulate data collection burden for healthcare-related data based on patient circumstances. Healthcare-related data may be data related to the prevention, treatment or management of a physical or mental illness. Such data may be directly used to prevent, treat or manage disease, or may include data that may be analyzed for healthcare reasons Benefits of modulating data collection may include making more data available to patients and physicians during salient events, reducing patient burden when it is not needed, and increasing patient compliance as they do not feel overly burdened by platform.

Various embodiments provide at least one data collection platform that is configured to modulate the resolution of data collection based on event(s). Data collection resolution connotes an amount of data and frequency of retrieval, where a higher resolution corresponds to more data at a greater frequency and a lower resolution corresponds less data at a smaller frequency. Data resolution may be modified by changing how often a data type is collected (e.g., instances of data collection) and/or may be modified by changing data types and/or a number of the data types that are collected. The term "data collection platform" generally refers to technology (e.g., a combination of hardware, firmware and software) that provides a set of capabilities for collecting data that can be used by the system. A data collection platform may be a single data collection platform or may be organized as more than one data collection platform that are configured to cooperate with each other. A data collection platform may be on one device or may be distributed among more than one device in the system. Thus, for example, a therapy device such as an implanted neuromodulator may provide some of the collected data, and a user device with a user interface may provide other of the collected data. A data collection platform may include sensor(s) and other data source(s). A data collection platform may, among other functions, allow data to be collected and served to users or applications. By way of example and not limitation, the data collection platform may modulate the resolution of data collection by asking a user if the frequency of data collection should be reduced, or asking if some event happened based on sensed data.

FIG. 1 illustrates, by way of example, an embodiment of a monitoring system 100 configured for use to collect healthcare-related data for transfer to a data receiving system. The illustrated monitoring system 100 is configured to include at least one data collection platform 101, an event detector 102, and a data output 103. The data collection platform(s) 101 is configured to collect healthcare-related data and the data output 103 is configured to transfer at least some of the collected data, as illustrated at 104, to a data receiving system 105. The data receiving system 105 may include one or more server(s) or other systems remotely located from the patient. Thus, the data transfer may use various network protocols to communicate and transfer data through one or more networks which may include the Internet. The data collection platform(s) 101 may include at least one processor configured to execute instructions stored in memory (e.g., illustrated as processor(s)/memory) to enable data input(s) 107 for receiving or collecting healthcare data 108, to provide a data resolution 109 for controlling the amount of data collected via the data input(s) 107, and a data resolution control 110 for changing or modulating the data resolution 109, which changes how data is collected. The event detector(s) 102 is configured for detecting event(s). The data resolution control 110 may be configured to respond to the detection of one or more events by changing the data resolution. By way of example and not limitation, each detected event may correspond to a specific data resolution for a predefined period of time or until the detect event stops or until another event occurs. The event detector 102 may detect event(s) using sensor(s), using user input(s), using a timer or clock, using indicator(s) of device usage, patient compliance with data collection and/or therapy, or various combinations thereof. Examples of healthcare data 108 may include patient data 111, medical device data 112, patient environmental data 113, therapy data 114, or various combinations thereof. The patient data 111 may include objective data 115 such as data collected from physiological sensor(s) and subjective data 116 such as data collected from user-answered question(s) (e.g., "How do you rate your pain?").

Figure 2:
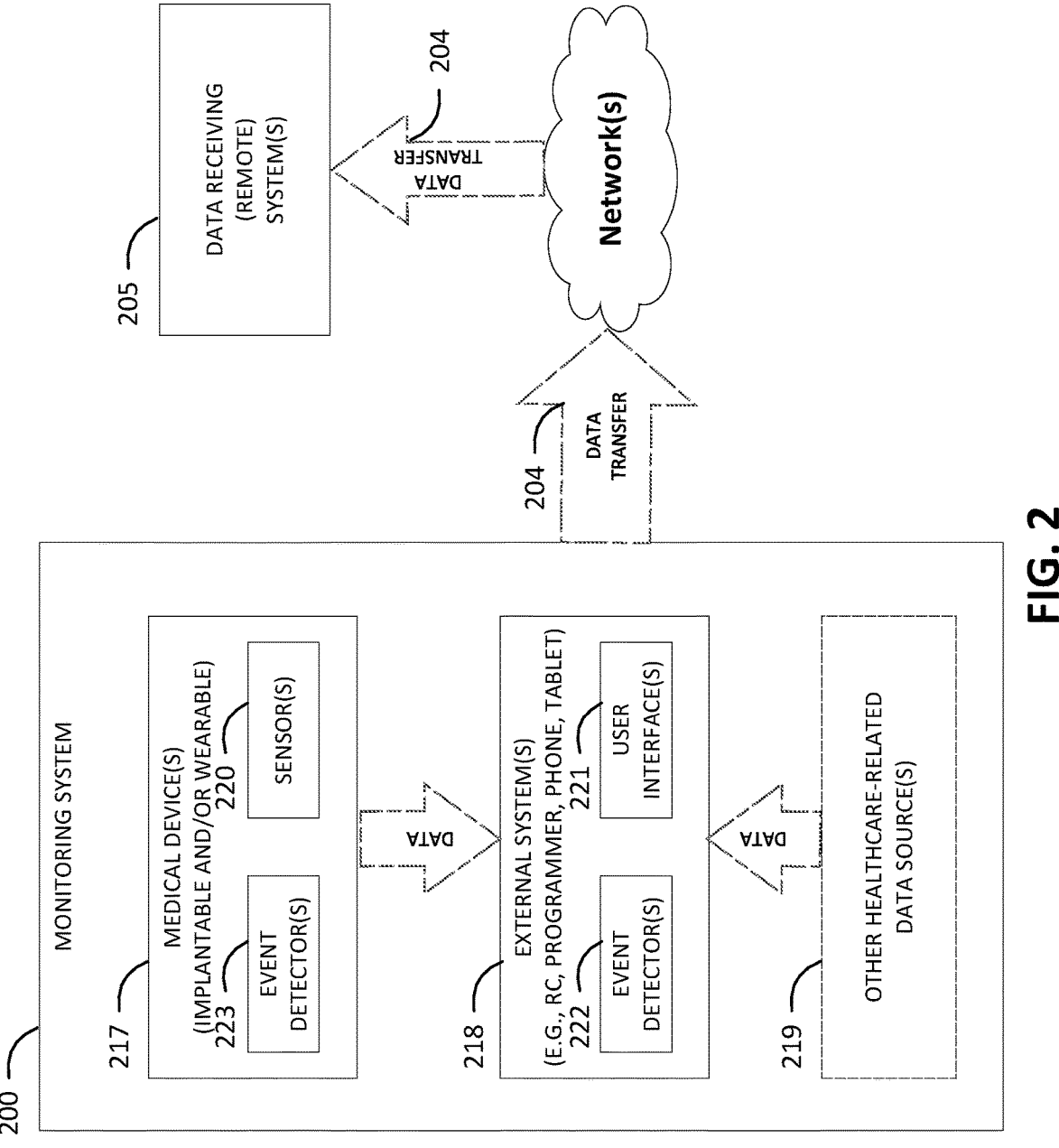
FIG. 2 illustrates, by way of example, an embodiment of a monitoring system that may include medical device(s), external system(s) or other health-care related data source(s) configured for use to collect healthcare-related data for transfer to a data receiving system.

FIG. 2 illustrates, by way of example, an embodiment of a monitoring system 200 that may include medical device(s) 217, external system(s) 218 or other healthcare related data source(s) 219 configured for use to collect healthcare-related data for transfer to a data receiving system. One or more of the medical device(s) 217, external system(s) 218 or other healthcare-related data source(s) 219 may include technology used by the system to collect data, and thus may form part of the data collection platform. The data collection platform may be on one device or may be distributed among more than one device in the system. The monitoring system 200 may include more than one medical device configured to communicate with each other or to an external system. Examples of medical devices 217 include implantable and wearable devices. The medical device may be configured to only collect data, to only deliver therapy, or to both collect data and deliver therapy. In the illustrated embodiment, the medical device includes sensor(s) 220 configured for use to collect patient data (e.g., objective patient data). The medical device may be configured to collect and provide medical device data such as device model, configuration, settings, and the like. Thus, the medical device may be configured to collect patient data 111, medical device data 112, environmental data 113, and therapy data 114 such as stimulation settings (see, for example, FIG. 1). Examples of external system(s) include remote controls, programmers, phones, tablets, smart watches, personal computers, and the like. In the illustrated embodiment, the external system(s) include at least one user interface 221 configured for use to receive user input, which may include user answers to questions. The user answers received via the user interface(s) 221 may include subjective patient data (e.g., "How do you rate your pain?" or "Where do you feel pain?") or objective patient data (e.g., "What is your heart rate?", "What is your blood pressure?", or "When did you fall asleep and wake up?"). The external system may be configured to collect medical device data 112 from the medical device 217. The external system may be configured to collect environmental data. 113 or therapy data 114. The monitoring system 200 may incorporate at least one event detector 222 into at least one of the external systems 218, may incorporate at least one event detector 223 into at least one of the medical devices 217, or may incorporate at least one event detector 222 into at least one of the external systems 218 and at least one event detector 223 into at least one of the medical devices 217.

Other healthcare-related data source(s) may include patient data received via a provider's server that stores patient health records. For example, patients may use a patient portal to access their health records such as test results, doctor notes, prescriptions, and the like. Other healthcare-related data sources may include various apps on a patient's phone or other device, or the data on a server accessed by those apps. By way of example and not limitation, this type of data may include heart rate, blood pressure, weight, and the like collected by the patient in their home, may include glucose measurements from a continuous glucose monitor. In another example, an app on a phone or patient's device may include or may be configured to access environmental data such as weather data and air quality information or location elevation data such as may be determined using cellular networks and/or a global positioning system (GPS). Weather data may include, but is not limited to, barometric pressure, temperature, sunny or cloud cover, wind speed, and the like.

The monitoring system 200 is configured to transfer data 204 via at least one network 224. The data transfer may use various network protocols to communicate and transfer data through one or more networks which may but does not necessarily include the Internet and/or various wireless networks, which may include short range wireless technology such as Bluetooth. The data may be transferred directly from at least one of the external systems and/or may be transferred directly from at least one of the medical device (s). As illustrated, the external system(s) 218 may be configured to receive data from the medical device(s) and/or receive data from other healthcare-related data source(s), and then transfer the data through the network(s) to the data receiving system(s) 205.

Figures 3, 4:
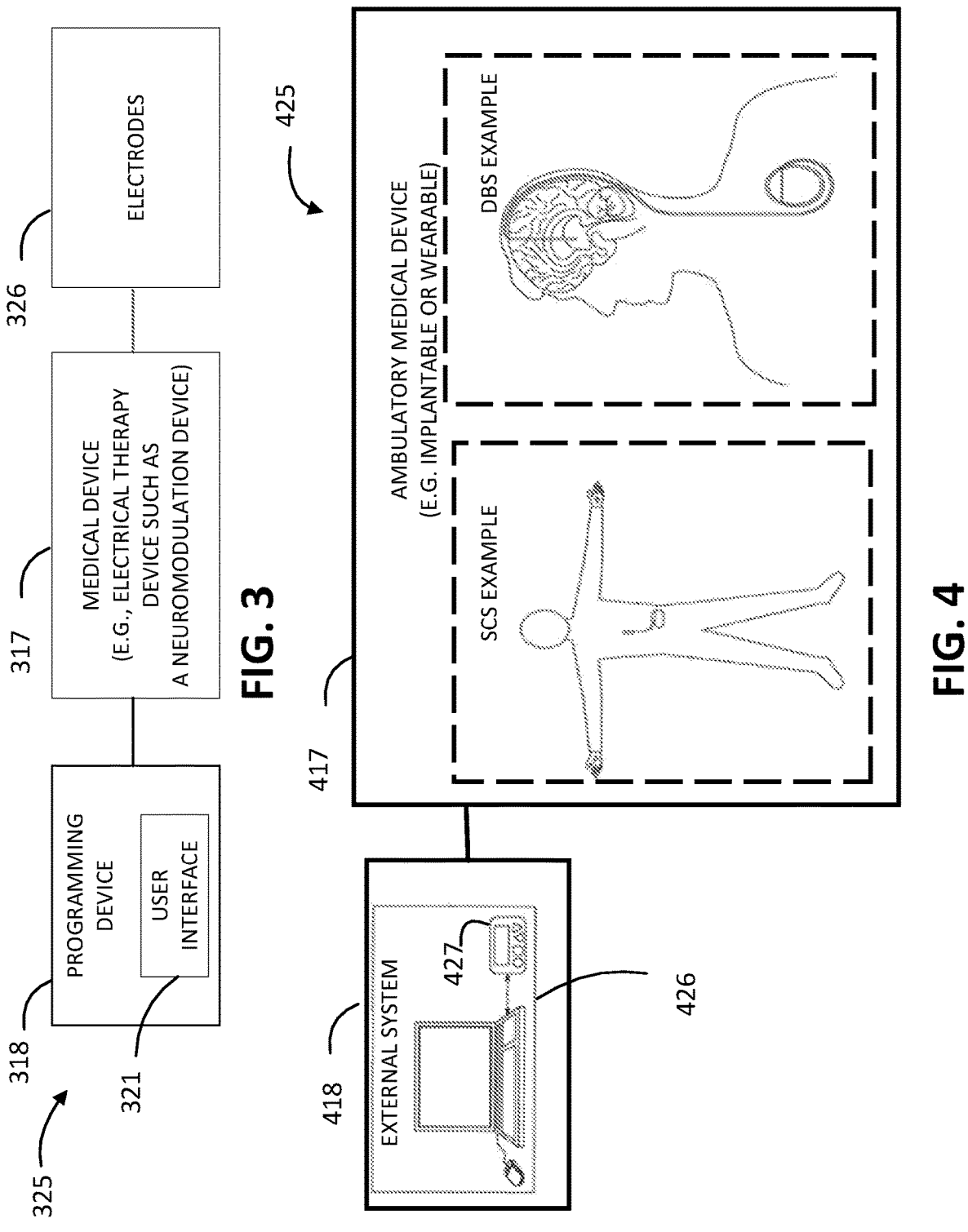
FIG. 3 illustrates a neuromodulation system as an example of a medical device system.
FIG. 4 illustrates, by way of example and not limitation, the neuromodulation system of FIG. 3 implemented in a spinal cord stimulation (SCS) system or a deep brain stimulation (DBS) system.

FIG. 3 illustrates a neuromodulation system as an example of a medical device system. The medical device 317 may be configured, by way of example and not limitation, to deliver an electrical therapy using electrode 326. In the illustrated embodiment, the medical device may be a neuromodulation device, and the system may be a neuromodulation system 325.

The illustrated neuromodulation system 325 includes electrodes 326, the neuromodulation device 317 and a programming system such as a programming device 318. The programming system may include multiple devices. The electrodes 326 are configured to be placed on or near one or more neural targets in a patient. The neuromodulation device 317 is configured to be electrically connected to electrodes 326 and deliver neuromodulation energy, such as in the form of electrical pulses, to the one or more neural targets though electrodes 326. The system may also include sensing circuitry to sense a physiological signal, which may but does not necessarily form a part of neuromodulation device 317. The delivery of the neuromodulation is controlled using a plurality of modulation parameters that may specify the electrical waveform (e.g., pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 318 provides the user with accessibility to the user-programmable parameters. The programming device 318 may also provide the use with data indicative of the sensed physiological signal or feature(s) of the sensed physiological signal. In various embodiments, the programming device 318 is configured to be communicatively coupled to modulation device via a wired or wireless link. In various embodiments, the programming device 318 includes a user interface 321 such as a graphical user interface (GUI) that allows the user to set and/or adjust values of the user-programmable modulation parameters. The user interface 321 may also allow the user to view the data indicative of the sensed physiological signal or feature(s) of the sensed physiological signal and may allow the user to interact with that data. The data collection platform may be on one device or may be distributed among more than one device in the system. Thus, for example, the medical device 317 and programming device 318 may contribute to the data collection platform for the neuromodulation system 325. The user interface 321 may be used to allow the user to answer questions to provide healthcare-related data. The electrode selection and other therapy parameters may also provide healthcare-related data. Additional sensor(s) may also provide healthcare-related data.

FIG. 4 illustrates, by way of example and not limitation, the neuromodulation system of FIG. 3 implemented in a spinal cord stimulation (SCS) system or a deep brain stimulation (DBS) system. The illustrated neuromodulation system 425 includes an external system 418 that may include at least one programming device. The illustrated external system 418 may include a clinician programmer 426 configured for use by a clinician to communicate with and program the neuromodulator, and a remote control 427 configured for use by the patient to communicate with and program the neuromodulator. For example, the remote control device may allow the patient to turn a therapy on and off and/or may allow the patient to adjust patient-programmable parameter (s) of the plurality of modulation parameters. FIG. 4 illustrates a medical device as an ambulatory medical device 417. Examples of ambulatory devices include wearable or implantable neuromodulators. The external system 418 may include a network of computers, including computer(s) remotely located from the ambulatory medical device 417 that are capable of communicating via one or more communication networks with the programmer 426 and/or the remote control 427. The remotely located computer(s) and the ambulatory medical device 417 may be configured to communicate with each other via another external device such as the programmer 426 or the remote control 427. The remote control device 426 and/or the programmer 426 may allow a user (e.g., patient and/or clinician or rep) to answer questions as part of the data collection process. The ambulatory medical device may include internal or external sensors that may be used to collect data, which may form at least part of the healthcare-related data to be transferred to a data receiving system. Parameter data for the programmed therapy may form at least part of the healthcare-related data to be transferred to a data receiving system.

Figures 5, 6:
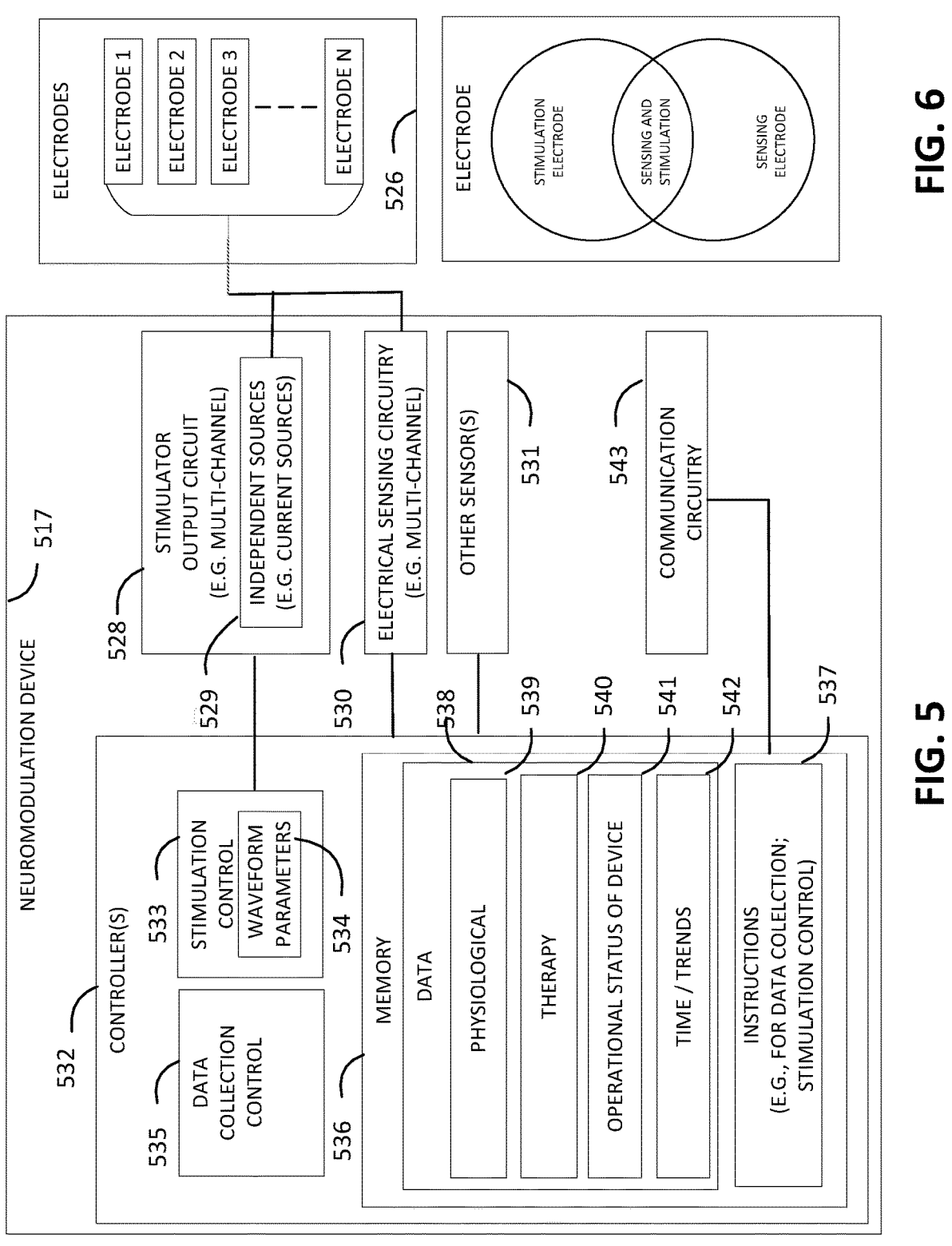
FIG. 5 illustrates, by way of example, an embodiment of a neuromodulation device, such as may be implemented as the medical device illustrated in FIGS. 2 and 3.
FIG. 6 is a diagram illustrating a relationship between a stimulation electrode and a sensing electrode.

FIG. 5 illustrates, by way of example, an embodiment of a neuromodulation device, such as may be implemented as the medical device illustrated in FIGS. 2 and 3. The modulation device 517 may be configured to be connected to electrode(s) 526, illustrated as N electrodes. Any one or more of the electrodes 526 may be configured for use to deliver modulation energy, sense electrical activity, or both deliver modulation energy and sense electrical activity. The modulation device 517 may include a stimulator output circuit 528 configured to deliver modulation energy to electrode(s). The stimulator output circuit 528 may be configured with multiple (e.g., two or more) channels for delivering modulation energy, where each channel may be independently controlled with respect to other channel(s). For example, the stimulator output circuit 528 may have independent sources 529 such as independent current sources or independent voltage sources. The modulation device 517 may include electrical sensing circuitry 530 configured to receive sensed electrical energy from the electrode(s), such as may be used to sense electrical activity in neural tissue or muscle tissue. The sensing circuitry may be configured to process signals in multiple (e.g., two or more) channels. By way of example and not limitation, the electrical sensing circuitry 530 may be configured to amplify and filter the signal(s) in the channel(s). The controller 532 may be configured to detect one or more features in the sensed signals. Examples of features that may be detected include peaks (e.g., minimum and/or maximum peaks including local peaks/inflections), range between minimum/maximum peaks, local minima and/or local maxima, area under the curve (AUC), curve length between points in the curve, oscillation frequency, rate of decay after a peak, a difference between features, and a feature change with respect to a baseline. Detected feature(s) may be fed into a control algorithm, which may use relationship(s) between the feature(s) and waveform parameter(s) to determine feedback for closed-loop control of the therapy. Some embodiments of the modulation device 517 may include or be configured to receive data from other sensor(s) 531. The other sensor(s) 531 may include physiological sensor(s), environmental sensor(s), or proximity sensor(s). The modulation device 517 may include a controller 532 operably connected to the stimulation output circuit 528 and the sensing circuitry 530, 531. The controller 532 may include a stimulation control 533 configured for controlling the stimulator output circuit 528. For example, the stimulation control 533 may include start/stop information for the stimulation and/or may include relative timing information between stimulation channels. The stimulation control 533 may include waveform parameters 534 that control the waveform characteristics of the waveform produced by the stimulation output circuit 528. The waveform parameters 534 may include, by way of example and not limitation, amplitude, frequency, and pulse width parameters. The waveform parameters 534 may include, by way of example and not limitation, regular patterns such as patterns regularly repeat with same pulse-to-pulse interval and/or irregular patterns of pulses such as patterns with variable pulse-to-pulse intervals. The waveform parameters may, but do not necessary, define more than one waveform shape (e.g., including a shape other than square pulses with different widths or amplitudes). The stimulation control 533 may be configured to change waveform parameter(s) (e.g., one or more waveform parameters) in response to user input and/or automatically in response to feedback.

The controller 532 may include a data collection control 535 configured for use by the neuromodulation device 517, and the data collection platform 101 of a monitoring system 100, 200 (see FIGS. 1-2), to collect healthcare related data. The controller 532 may include a memory 536 with instructions 537 for use to control the data collection using the data collection control 535 and control the stimulation via the stimulation control 533. The memory may also include storage for storing different types of collected healthcare-related data 538, such as physiological data 539, therapy data 540, data regarding the operational status of the device 541, and times/trends for data 542. Examples of physiological data 539 may include, by way of example and not limitation, heart rate, heart rate variability, oxygen saturation, activity, posture, steps, gait, temperature, evoked compound action potentials (ECAPS), electromyograms (EMGs), electroencephalograms (EEGs), weight, blood pressure, and the like. Examples of therapy data 540 may include, by way of example and not limitation, stimulations settings such as amplitude, pulse width, pulse frequency period, duration of burst of pulses, active electrodes, electrode fractionalization controlling the distribution of energy (e.g., current) to active electrodes, waveforms, pulse patterns including various complex patterns, and the like. Examples of data regarding the operational status of the device 541 may include, by way of example and not limitation, electrode-tissue impedance, fault conditions, battery information such as battery health, battery life, voltage, charge state, charging history if rechargeable, MRI status, Bluetooth connection logs, connection with Clinician Programmer, hours of operation/duration of implant, and the like. Other device information may include device model and lead model. Examples of time or trend data 542 may include changes (e.g., increases and/or decreases) in activity, pain, function and sleep. The neuromodulation device may include communication circuitry 543 configured for use to communicate with other device(s) such as a programmer, remote control, phone, tablet and the like. The healthcare-related data may be transferred out from the neuromodulation device for transfer to a data receiving system.

FIG. 6 is a diagram illustrating a relationship between a stimulation electrode and a sensing electrode. The stimulation electrode is configured for use in delivering modulation energy, and the sensing electrode is configured for use in sensing electrical activity. As illustrated, the stimulation electrode may also be used in sensing electrical activity, and the sensing electrode may also be used in delivering modulation energy. Thus, the term "stimulation electrode" does not necessary exclude the electrode from also being used to sense electrical activity; and the term "sensing electrode" does not necessarily exclude the electrode from also being used to deliver modulation energy.

FIG. 7 illustrates, by way of example, a method for changing data resolution for collecting healthcare-related data in response to an event. The illustrated method may include collecting healthcare-related data at a defined data resolution (illustrated as "present resolution(s)") for transfer to a data receiving system 744, detecting an event 745, and responding to the detected event by changing the data resolution for collecting healthcare-related data 746. If the event is not detected at 745, the method may continue to collect healthcare-related data at the defined data resolution 744. An example of an event that could trigger changes in data collection may be an end of a time period, such as an end of a baseline period of time for collecting data. For example, once data is collected for the baseline period of time, the method may reduce the collected data under an assumption that the data will not significantly change until a subsequent event occurs. However, when the subsequent event occurs, the data resolution for collecting data may change again. Other examples of events may include a significant increase or decrease in pain levels, significant changes in activity, sleep, mood or medication use, multivariate changepoint detection, a change in the patient's compliance for responding to questions, a request from the patient or other user to increase data resolution (e.g., data collection frequency) for a variety of reasons such as, but not limited to, an upcoming significant event or events. Examples of such upcoming significant events may be, but are not limited to, significant travel days, holidays, surgery or a clinical visit. The event may be based on the ability for the patient to upload data from their implantable medical device or other device. A frequency for requesting the patient to upload data may be changed based on how willing the patient is to sit for the upload process. For example, if a patient is willing to sit longer to upload the healthcare-related data, the frequency for requesting the patient to upload data may be reduced.

Prior use patterns may be used to determine the characteristics for future data collection. The event detector may be configured to detect patient engagement with at least one user interface used to receive data from the patient. For example, the system may acquire data from a patient by the patient interacting with their smartphone device. Different people interact with their devices in different ways, at different times. Some have patterns of use that they consistently follow, and others may have more sporadic patterns of device usage. Some embodiments may learn the use patterns and then adjust the data input requirements based on the learned use patterns. The change to the data resolution may include a change to timing for asking at least one subjective question or a question type for asking the at least one subjective question. By way of example, the detected event may relate to the patient's routine for interacting with their mobile device or patient app (e.g., learned by observing patient's use of device) to make data collection fit into their routine. For example, if a user typically uses their phone between the times of 6:00 AM to 7:00 AM as they prepare for work, then the data requirements, processing, notifications and/or reminders may be tailored to that time. Any of the number of questions, the type or questions, the expected length required to answer questions or the time for answering may change based on the patient's routine. For example, if the compliance of the patient in answering questions is diminished, then the system may request fewer questions or at least questions that are easier and faster to answer. The system may learn that the patient is more likely to comply with answering questions if the questions are presented at time(s) of day when the system determined that the patient is more engaged. The system may be configured to adjust the data resolution for collecting data to reasonably correspond to the patient's expectations, where the patient's expectations may be expressly provided by the patient or may be learned by the system based on the patient's behavior. By way of example and not limitation, the data resolution for collecting data may be modulated by reducing or increasing the frequency of patient-reported output questions. Non-limiting examples may include changing data collection from twice daily to weekly, from weekly to greater than twice daily, from daily to hourly, and the like. The data resolution for collecting data may be modulated by reducing or increasing a frequency for triggering of physiological data collection. A non-limiting example includes changing from triggering physiological data collection from twice daily to weekly. The data resolution for collecting data may be modulated by reducing or increasing a sampling rate for collecting physiological data from sensors(s). A non-limiting example includes changing how often heart rate data is collected (e.g., changing from collecting heart rate for every one or every few beats to collecting a daily heart rate). The data resolution for collecting data may be modulated by reducing or increasing a rate of data upload requests (e.g., from daily upload requests to weekly upload requests). The resolution for collecting data may be modulated by adjusting a recall period of questions depending on a frequency of triggering the questions. For example, the same question or different questions may be asked depending on sampling rate at any one time. The resolution for collecting data may be modulated by changing the type of questions presented to the patient (e.g., questions with multiple choice answers or free text answers). For example, if the patient only responds to multiple choice question or only responds to free text questions, then only multiple-choice questions or only free text questions may be presented to the patient.

The event may related to patient activity. For example, if it is determined that the patient is moving more than a threshold, then more activity data may be collected. If the patient is more engaged on an app on the patient's phone, such as may be determined by time on a page or based on taps by the patient, then more questions may be presented by the patient.

The event may be any change that crosses a threshold to indicate that that change is significant, and more information is desired to interpret or analyze the event or other data (e.g., therapy data) in view of the event. More data may be requested when there has been a significant change (good or bad) so that the effect of the event may be better understood.

Some embodiments may account for other requirements for data outside of patient burden before reducing it, such as what is needed to physician calculations or reimbursement. Some embodiments switch between data type. For example, the system may be configured to switch between subjective and objective data for a patient. For instance, if pain models can accurately predict pain, then the system does not ask for pain score. Similarly, if sleep quality/duration can be accurately detected, then the system does not ask questions concerning sleep quality. This could apply to other data streams as well. Some systems may be configured with data imputation. Successful data imputation may be used as an input for determining how intently the system prompts the patient for data. For example, more data collection may be desirable if reliable imputation is not possible. However, if reliable imputation is possible then the need to get additional data is less urgent.

FIG. 8 illustrates, by way of example, a method for pausing collection of healthcare-related data. The illustrated method may include collecting healthcare-related data at a defined data resolution (illustrated as "present resolution(s) ") for transfer to a data receiving system 844, and detecting an event 845. If the event is not detected at 845, the method may continue to collect healthcare-related data at the defined data resolution 844. When the event is detected at 845, the user or patient may be requested to determine whether to pause the data collection or to determine how long to pause the data collection 847. The data collection remains paused until the pause duration expires 848. After the pause duration expires, then the collection of healthcare-related data may be collected again at 844 either with the same resolution or a different resolution.

Figure 9:
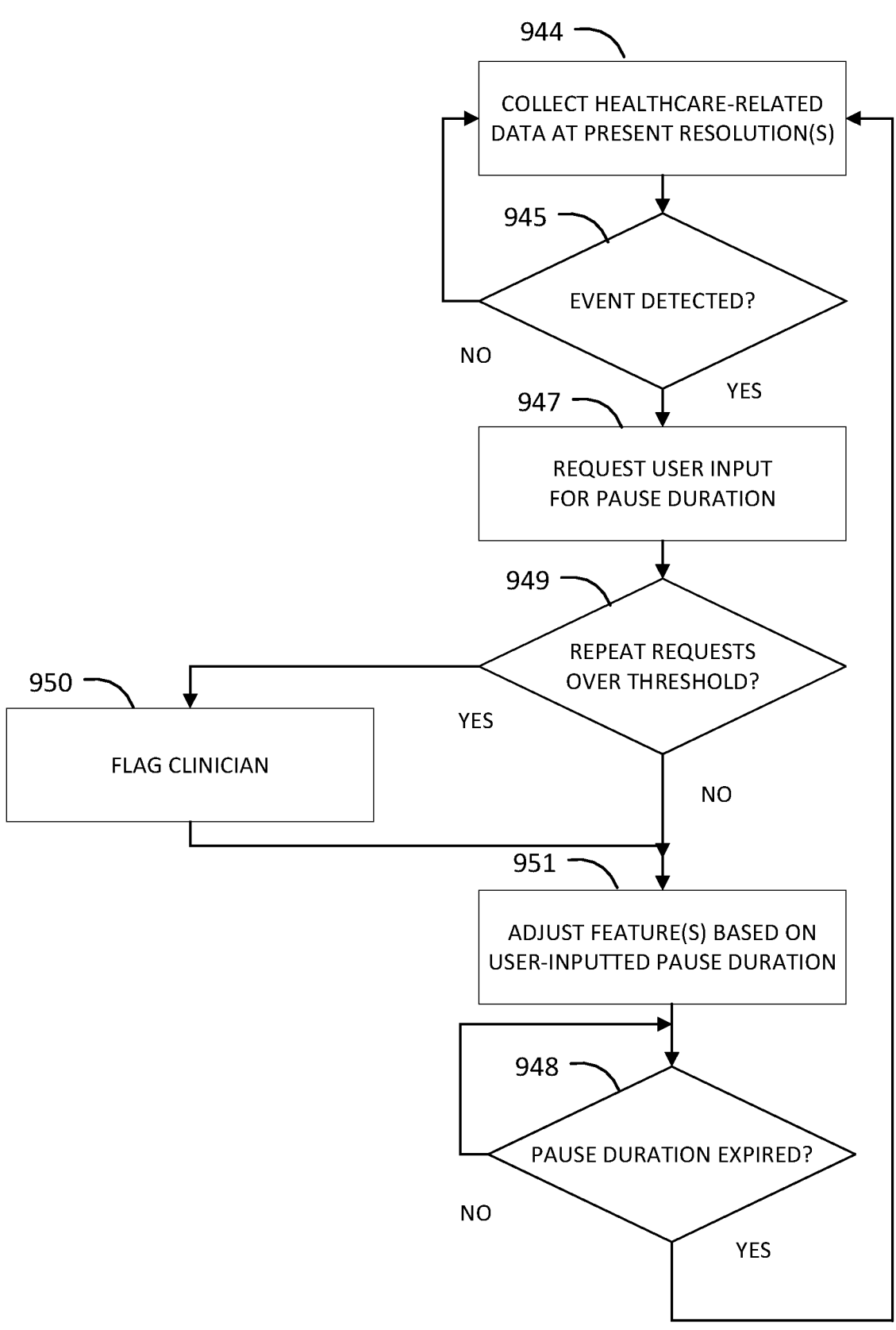
FIG. 9 illustrates, by way of example, a method for adjusting feature(s) of a healthcare system (e.g., therapy) based on a user-requested pause duration.

FIG. 9 illustrates, by way of example, a method for adjusting feature(s) of a healthcare system (e.g., therapy) based on a user-requested pause duration. The illustrated method may include collecting healthcare-related data at a defined data resolution (illustrated as "present resolution(s) ") for transfer to a data receiving system 944, and detecting an event 945. If the event is not detected at 945, the method may continue to collect healthcare-related data at the defined data resolution 944. When the event is detected at 945, the user or patient may be requested to determine whether to pause the data collection or to determine how long to pause the data collection 947. The system may be configured to, as illustrated at 949, determine whether the number of requests for pausing duration has exceeded a threshold. If the number of requests exceeds a threshold, then the clinician may be flagged, as illustrated at 950. As illustrated at 951, some embodiments may adjust feature(s) of the system based on the user-inputted pause duration. For example, some embodiments may deliver a more robust therapy (e.g., closed-loop v. open loop) if more data can be collected or may provide better suggestions or inferences if more data can be collected. The data collection remains paused until the pause duration expires 948. After the pause duration expires, then the collection of healthcare-related data may be collected again at 944 either with the same resolution or a different resolution. Thus, patients may have the option to pause data collection for whatever reason, while still having a strong incentive to resume data collection to have access to the disabled feature(s) of the system. By way of example and not limitation, features that may be disabled or limited if the tool is paused for too long could include: battery longevity predictions, closed-loop recommendations, closed-loop therapy adjustments or any plots of historical trends. After a long period of indefinite pausing, a flag may be raised to the clinician's office suggesting that the clinician contact the patient.

FIG. 10 illustrates, by way of example, a user interface for requesting a user to indicate whether the collection of healthcare-related data should be paused and the length of the pause, and to provide notice that feature(s) may be adjusted because of the user-requested pause. A patient's phone, tablet or remote control may provide the illustrated user interface. However, other devices may be used to provide the user interface. The user interface may be con-figured to ask if the patient would like to pause therapy tracking and optimization, and receive an answer from the user. For example, the answer may be received via a selection of a YES or NO button. However, the answer may be received using other techniques. The user interface may be further configured to ask for how long the patient would like the pause. This question may be on a separate screen as illustrated, or may be on the same screen. The user interface may, by way of example and not limitation, provide a multiple choice of durations. In the illustrated embodiment, the patient is presented with choices for selection, including "1 day"; "2 days", "3 days", "4 days" and "Indefinite." However, the answer may be provided using other tech-niques. The user interface may also provide a warning or notice, as illustrated at 1055, that certain features may be disabled immediately or after a time duration. A reason for the disabling of certain feature(s) may be that the feature(s) require data to be collected. The reason for the disabling of feature(s) may be presented to the patient. In FIG. 10, the displayed reason is "as data is required to power these tools."

FIG. 11 illustrates, by way of example and not limitation, a timeline for adjusting collection rates in response to various events. At the onset of remote patient monitoring ("RPM BEGINS" 1156), data may be collected at standard resolutions ("STANDARD COLLECTION RATE" 1157) for a baseline period (e.g., 2 weeks). A timer or clock may be used to determine when baseline period ends 1158. In response to the event that the baseline period ends 1158, the system may reduce the collection rate 1159. An event may be that the patient is experiencing pain greater than a threshold (e.g., >8). For example, the event may require that the pain is greater than a pain threshold for a length of time greater than a duration threshold (e.g., 2 days) 1160. The event criteria may be pain greater than a pain threshold for a cumulative amount of time (e.g., 24 hours) over a duration of two days. In response to the pain event 1160, the system may increase the collection rate 1161. An event may be a detected reduction in the patient complying with questions ("REDUCED QUESTION COMPLIANCE" 1162). The event criteria may be reduced compliance over a period of time (e.g., a week). In response to the detection of the reduced question compliance 1162, the system may reduce the collection rate 1163. An event may be high activity by the patient 1164. By way of example, activity may be determined using sensor(s) such as accelerometers, proxim-ity sensor(s) indicating that a patient is near one of the proximity sensor(s) and consequently, not near one of the proximity sensor(s), location sensors such as location detec-tors on a phone based on GPS or wireless network signals. The event detection criteria may be activity over a threshold for a period for a period of time (e.g., week) or over a threshold for a cumulative time (e.g., 4 hours) during a duration (e.g., day). In response to the high activity event 1164, the system may increase the collection rate 1165. Thus, the system is able to appropriately modulate the collection rate in response to various events to obtain more data when desirable to explain significant changes and to lower the collection rate if patient compliance is reduced or if it is otherwise determined that additional data is not likely to provide significant information. such as may occur when there is very little change occurring. The timeline and specific events in the timeline are provided as nonlimiting examples. The system may be configured to detect and respond to other events, and the collection resolution may be changed in other ways in response to various events.

Figure 12:
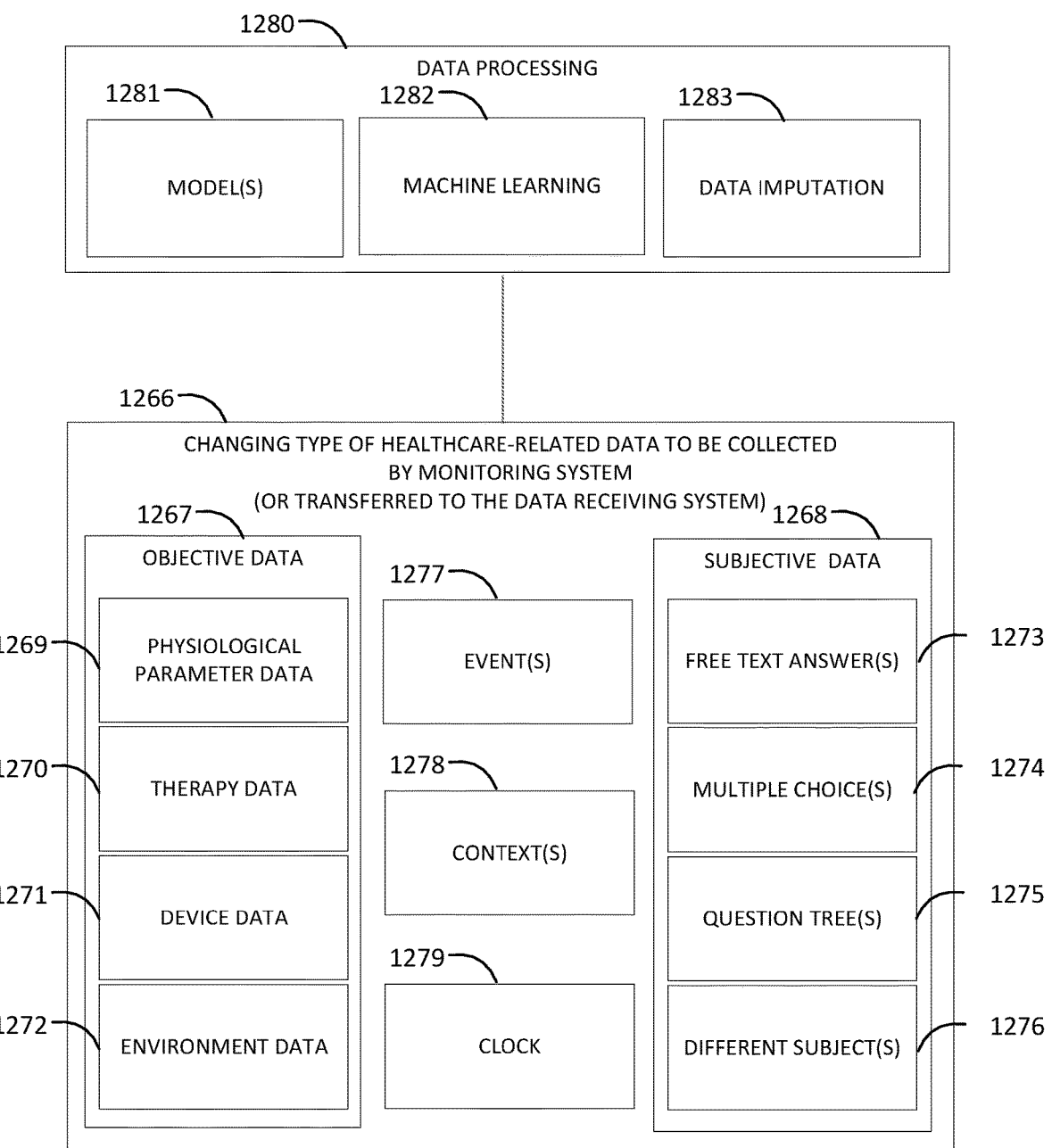
FIG. 12 illustrates, by way of example, healthcare-related data types that may be available to be added or removed from data collection or transfer, and/or whose number of collection instances over a period of time (e.g., collection rate) may be increased or decreased.

FIG. 12 illustrates, by way of example, healthcare-related data types that may be available to be added or removed from data collection or transfer, and/or whose number of collection instances over a period of time (e.g., collection rate) may be increased or decreased. The healthcare-related data types 1266 may include objective data 1267 and subjective data 1268.

Objective data 1267 is data that can be observed using our senses, and may be obtained from a measurement or direct observation. Objective data may be measured by a sensor and may be provided via user input when the user has access to objectively determined information. Examples of objec-tive data 1267 may include physiological parameter data 1269, therapy data 1270, device data 1271, and environ-mental data 1272. By way of example and not limitation, physical parameter data 1269 may include data such as: heart rate, blood pressure, respiration rate, activity, posture, electromyograms (EMGs), neural responses such as evoked compound action potentials (ecaps), glucose measurements, oxygen levels body temperature, oxygen saturation and gait. By way of example and not limitation, therapy data 1270 may include: neuromodulation programs, therapy on/off schedule, dosing, neuromodulation parameters such as waveform, frequency, amplitude, pulse width, period, therapy usage and therapy type. By way of example and not limitation, device data 1271 may include: battery informa-tion (voltage, charge state, charging history if rechargeable), impedance data, faults, device model, lead models, MRI status, Bluetooth connection logs, connection history with Clinician's Programmer (CP). By way of example and not limitation, environmental data 1272 may include: tempera-ture, air quality, pressure, location, altitude, sunny, cloudy, precipitation, etc. The modulation of data resolution may include increasing or decreasing the sensors used to obtain subjective data, may increase the number of times that sensor data is obtained over a given period of time (e.g., rate), or may change one type of sensor for another type of sensor. The modulation of data resolution may include adding or removing at least one of physiological parameter data, therapy data, device data or environment data in response detected event(s).

Subjective data 1268 includes information received from the patient. For example, the patient's quantification of pain is a subjective data. Subjective data may generally involve user-inputted data. Examples of subjective data include questions with free text answers 1273, multiple choice questions 1274, question tree(s) 1275, and different question subject(s) 1276. The data resolution may be modulated by changing the type of subjective data that is being received (e.g., adding or removing at least one of free text answers, multiple choice answers, question trees or subject of the question, and may be modulated by changing between objective and subjective data). The modulation of data resolution may include increasing or decreasing the number of times that subjective data is obtained over a given period of time (e.g., rate). the modulation of data resolution may change between obtaining subjective data and objective data.

Other data may be stored and/or transferred, including detected event(s) 1277 that trigger a response that changes data resolution, contextual data 1278 for other collected data and/or event(s), and a clock/time 1279 such as may be used to provide a time stamp associated with the retrieved data. The event(s), context(s) and time may be detected by the system or may be provided via user input.

The collected data may be processed, as generally illustrated at 1280. The data processing may occur in a medical device or an external device (e.g., phone, tablet, remote control, programmer) by the patient, or may occur in a remote data receiving system. The data processing 1280 may include one or more model(s) 1281 which, by way of example and not limitation, may use the acquired data to deliver therapy or to determine disease progression or disease state. Machine learning 1281 may be implemented on the collected data to develop or refine the model(s). The data processing may include data imputation 1282, which refers to a process of replacing missing data with substituted values such as may be used to prevent missing data from introducing bias into the model(s) or machine learning. The data processing may provide control signals to the data collection platform to control modulation of the data resolution. For example, if the data imputation is effectively accurate, then the data resolution may not need to be modulated. However, if the data imputation is causing problems with the accuracy of the model(s) or machine learning, then the data resolution may be increased to provide more data and reduce the need to rely on data imputation. In another example, the machine learning may determine that some data is valuable and or may determine that other data is valuable, and thus may control the modulation of the data resolution.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks or cassettes, removable optical disks (e.g., compact disks and digital video disks), memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method performed using a medical system having an event detector and a data collection platform, comprising:

collecting subjective patient data by using at least one user interface to receive subjective patient data by requesting the patient to answer at least one question, wherein the subjective patient data is collected using the data collection platform for the medical system at a defined data resolution for transfer from the medical system to a data receiving system that includes one or more server(s) remotely located from the patient using at least one network, wherein the data collection platform includes one or more processors, at least one data input for receiving subjective patient data, and memory for storing instructions for implementation by the one or more processors to collect subjective patient data via the at least one data input and for storing the collected subjective patient data for transfer to the data receiving system;

detecting an event using the event detector for the medical system, wherein the detecting the event includes detecting patient compliance with providing the subjective patient data or detecting patient engagement with the at least one user interface used to receive subjective patient data from the patient; and responding to the detected event, using the one or more processors of the data collection platform, wherein the one or more processors respond to the detected event by changing the data resolution, pausing collection of the subjective patient data and requesting and receiving user input for a user-requested pause duration for the pausing the collection of the subjective patient data, wherein the one or more processors of the data collection platform pause the collection of the subjective patient data until the pause duration expires, wherein the data resolution is changed by at least one of:

changing a number of questions to be answered by the patient;

changing a type of question to be answered by the patient; or changing at least one of timing or a question type for asking at least one subjective question; and wherein, based on the user-requested pause duration, the one or more processors, automatically transmit a flag to a clinician using the at least one network and automatically adjust one system feature including at least one system feature by disabling battery longevity predictions, disabling closed-loop recommendations, disabling closed-loop therapy adjustments, or disabling plots of historical trends when the user-requested pause duration exceeds a threshold or when a number of patient-requested pauses exceeds a threshold.

2. The method of claim 1, wherein the changing the data resolution includes increasing or decreasing the number of questions to be answered by the patient.

3. The method of claim 1, wherein the changing the data resolution includes changing the type of question to be answered by the patient.

4. The method of claim 1, wherein the changing the data resolution includes increasing or decreasing a number of data-collection instances over a period of time.

5. The method of claim 1, wherein the changing the data resolution includes switching from collecting at least some of the subjective patient data to collecting sensor data.

6. The method of claim 1, wherein:
the changing the data resolution includes changing a number of sensors used to detect the sensor data or replacing at least one sensor used to detect the sensor data.

7. The method of claim 1, wherein the medical system includes a medical device configured to deliver a therapy and at least one of a phone, a tablet, a computer, or a smart watch configured to provide the at least one user interface used to receive subjective patient data by requesting the patient to answer at least one question.

8. The method of claim 7, wherein the medical device includes an implantable medical device configured to be electrically connected to one or more electrodes to deliver the therapy to a biological target.

9. The method of claim 8, wherein the implantable medical device comprises a neuromodulation device.

10. The method of claim 1, wherein the changing the data resolution includes changing at least one of timing or a question type for asking at least one subjective question.

11. The method of claim 1, further comprising collecting, using the data collection platform, data related to operational status of a medical device, data related to a therapy provided by a medical device, or patient environmental data acquired by at least one external sensor or acquired from an environmental data source.

12. The method of claim 1, further comprising transferring the collected subjective patient data to the data receiving system and transferring at least one of the detected event, or contextual information, or a time associated with at least some collected subjective patient data with the collected subject patient data.

13. A non-transitory machine-readable medium including instructions, which when executed by a medical system having an event detector and a data collection platform, cause the medical system to perform a method comprising:
collecting subjective patient data by using at least one user interface to receive subjective patient data by requesting the patient to answer at least one question, wherein the subjective patient data is collected using the data collection platform for the medical system at a defined data resolution for transfer from the medical system to a data receiving system that includes one or more server(s) remotely located from the patient using at least one network, wherein the data collection platform includes one or more processors, at least one data input for receiving subjective patient data, and memory for storing instructions for implementation by the one or more processors to collect subjective patient data via the at least one data input and for storing the collected subjective patient data for transfer to the data receiving system;

detecting an event using the event detector for the medical system, wherein the detecting the event includes detecting patient compliance with providing the subjective patient data or detecting patient engagement with at least one user interface used to receive subjective patient data from the patient;
responding to the detected event, using the one or more processors of the data collection platform, wherein the one or more processors respond to the detected event by changing the data resolution, pausing collection of the subjective patient data, and requesting and receiving user input for a user-requested pause duration for a pause in collecting healthcare data, and pausing the collection of the subjective patient data until the pause duration expires,
wherein the data resolution is changed by at least one of:
changing a number of questions to be answered by the patient;
changing a type of question to be answered by the patient; or
changing at least one of timing or a question type for asking at least one subjective question; and
wherein, based on the user-requested pause duration, the one or more processors automatically transmit a flag to a clinician using the at least one network and automatically adjust one system feature including at least one system feature by disabling battery longevity predictions, disabling closed-loop recommendations, disabling closed-loop therapy adjustments, or disabling plots of historical trends when the user-requested pause duration exceeds a threshold or when a number of patient-requested pauses exceeds a threshold.

14. The non-transitory machine-readable medium of claim 13, wherein the changing the data resolution includes at least one of:
increasing or decreasing the number of questions to be answered by the patient;
changing the type of question to be answered by the patient; or
increasing or decreasing a number of data-collection instances.

15. A system, comprising:
at least one data collection platform configured for use to collect subjective patient-data by using at least one user interface to receive subjective patient data by requesting the patient to answer at least one question, wherein the subjective patient data is collected at a defined data resolution for transfer from the at least one data collection platform to a data receiving system that includes one or more server(s) remotely located from the patient using at least one network, the at least one data collection platform including one or more processors, at least one user interface for receiving subjective patient data, and memory for storing instructions for implementation by the one or more processors to collect subjective patient data via the at least one user interface; and
an event detector configured to detect an event, wherein the event is detected by detecting patient compliance with providing the subjective patient data or detecting patient engagement with the at least one user interface used to receive subjective patient data from the patient,
wherein the one or more processors of the at least one data collection platform are configured to respond to the detected event by changing the data resolution, pausing collection of the subjective patient data, and requesting user input for a user-requested pause duration for a pause in collecting healthcare data, wherein, based on the user-requested pause duration, the one or more processors of the at least one data collection platform are configured to pause the collecting the subjective patient data until the pause duration expires, and are configured to automatically transmit a flag a clinician using the at least one network and automatically adjust one system feature including at least one system feature by disabling battery longevity predictions, disabling closed-loop recommendations, disabling closed-loop therapy adjustments, or disabling plots of historical trends when the user-requested pause duration exceeds a threshold or when a number of patient-requested pauses exceeds a threshold.

16. The system of claim 15, wherein the change to the data resolution includes an increase or a decrease in a number of questions to be answered by the patient.

17. The system of claim 15, wherein:

the change to the data resolution includes a type of questions to be answered by the patient.

18. The system of claim 15, wherein the change to the data resolution includes an increase or decrease in a number of data-collection instances.

19. The system of claim 15, wherein further including a medical device configured to deliver a therapy and at least one of a phone, a tablet, a computer, or a smart watch configured to provide the at least one user interface used to receive subjective patient data by requesting the patient to answer at least one question.

* * * * *